US00PP23596P3

(12) United States Plant Patent
Stemkens

(10) Patent No.: US PP23,596 P3
(45) Date of Patent: May 14, 2013

(54) ***VERBENA* PLANT NAMED 'VEAZ0003'**

(50) Latin Name: *Verbena×hybrida*
Varietal Denomination: VEAZ0003

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 85 days.

(21) Appl. No.: 13/317,220

(22) Filed: Oct. 11, 2011

(65) Prior Publication Data

US 2013/0091609 P1 Apr. 11, 2013

(51) Int. Cl.
*A01H 5/00* (2006.01)

(52) U.S. Cl.
USPC ..... Plt./308

(58) Field of Classification Search ..... Plt./308
See application file for complete search history.

*Primary Examiner* — Annette Para
(74) *Attorney, Agent, or Firm* — Joshua L. Price

(57) ABSTRACT

A new *Verbena* plant named 'VEAZ0003' particularly distinguished by the has light red to orange-red flower color; medium to dark green foliage, medium vigor, a creeping and trailing plant habit with good branching.

1 Drawing Sheet

Figure 1:
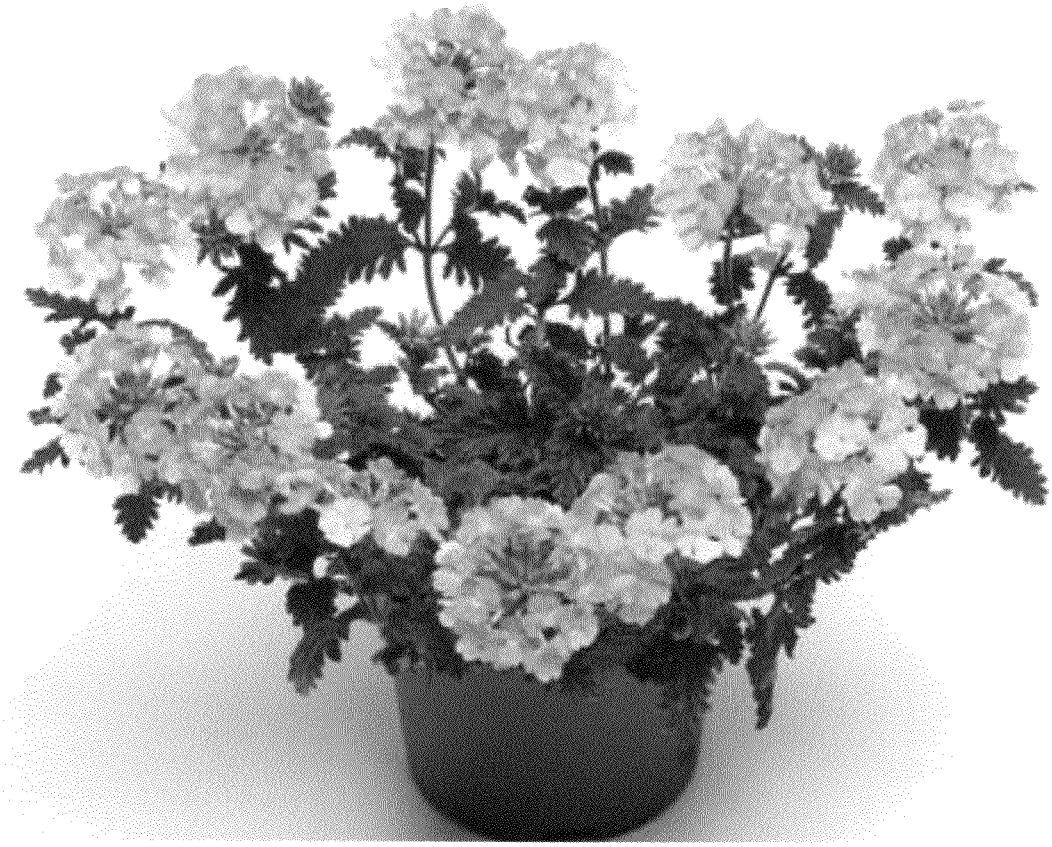
Figure 2:
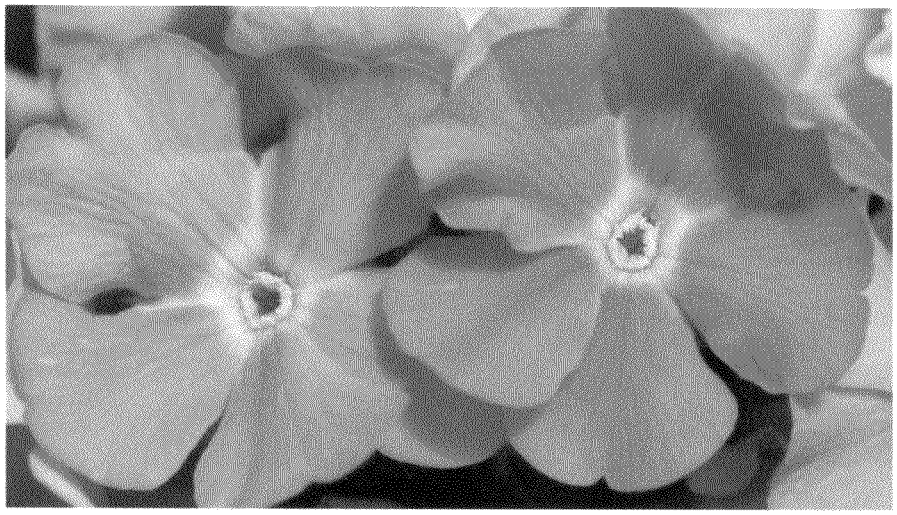

Latin name of the genus and species of the plant claimed: *Verbena×hybrida.*

Varietal denomination: 'VEAZ0003'.

BACKGROUND OF THE NEW PLANT

The present invention comprises a new *Verbena*, botanically known as *Verbena×hybrida*, and hereinafter referred to by the variety name 'VEAZ0003'.

'VEAZ0003' is a product of a planned breeding program. The new cultivar has light red to orange-red flower color, medium to dark green foliage, medium vigor, a creeping and trailing plant habit with good branching.

'VEAZ0003' originated from an open pollinated hybridization made in the summer of 2005 in a controlled breeding environment in Enkhuizen, Netherlands. The female parent was the unpatented, proprietary plant designated 'H0641-7' with small salmon colored flowers and light green foliage.

The male parent of 'VEAZ0003' was an unknown plant. The resultant seed was sown in February 2006.

'VEAZ0003' was selected as one flowering plant within the progeny of the stated cross in May 2006 in a controlled environment in Enkhuizen, Netherlands.

The first act of asexual reproduction of 'VEAZ0003' was accomplished when vegetative cuttings were propagated from the initial selection in May 2006 in a controlled environment in Enkhuizen, Netherlands.

BRIEF SUMMARY OF INVENTION

Horticultural examination of plants grown from cuttings of the plant initiated in May 2006, and continuing thereafter, has demonstrated that the combination of characteristics as herein disclosed for 'VEAZ0003' are firmly fixed and are retained through successive generations of asexual reproduction.

'VEAZ0003' has not been observed under all possible environmental conditions. The phenotype may vary significantly with variations in environment such as temperature, light intensity and day length.

Plant Breeder's Rights for this cultivar were applied for in Canada on Dec. 17, 2010, #10-7125 and in the Community Plant Variety Office on Oct. 20, 2010, #2010/2237. 'VEAZ0003' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawing shows typical flower and foliage characteristics of 'VEAZ0003' with colors being as true as possible with an illustration of this type. The photographic drawing shows a flowering potted plant of the new variety and a close-up of the flowers.

DETAILED BOTANICAL DESCRIPTION

The aforementioned photographs were taken in April 2010 from plants grown in a greenhouse trial in Enkhuizen, The Netherlands. These plants were growing in 12 cm pots and were approximately 12 weeks of age. The close-up photograph was taken in April, 2011 in Gilroy Calif. Plants were about 9-11 weeks of age, grown in a greenhouse breeder's trial.

The plant descriptions and measurements were taken in May 2011 in Enkhuizen, Netherlands on about 13 week old plants that had been planted into 12 cm pots and were grown on benches in a greenhouse at a minimum temperature (heating temperature) of 12° C. From April on, a minimum night temperature of 8° C. was held, while day temperatures were much higher, depending on outdoor temperature.

Color references are made to The Royal Horticultural Society Colour Chart (R.H.S.) 2001.

TABLE 1

DIFFERENCES BETWEEN THE NEW VARIETY 'VEAZ0003' AND A SIMILAR VARIETY

| | 'VEAZ0003' | 'Lan Peachy' (U.S. Plant Patent No. 15,536) |
|---|---|---|
| Leaf Color: | Darker green | Lighter green |
| Flower Color: | Darker | Lighter |

Plant:

*Form, growth and habit*.—Herbaceous, initially spreading, later becoming decumbent to trailing.

*Plant height*.—About 7.0 cm.

*Plant height* (*inflorescence included*).—About 14.0 cm.

*Plant width*.—About 44.0 cm.

Roots:

*Number of days to initiate and produce roots*.—About 10-14 days at about 22 degrees C.

*Type*.—Fine, fibrous, free branching.

*Color*.—RHS N155B.

Foliage:

*Arrangement*.—Opposite.

*Immature, leaf color, upper surface*.—RHS 137C.

*Lower surface*.—Between RHS 138B and RHS 138C.

*Mature, leaf color, upper surface*.—RHS 137A.

*Lower surface*.—RHS 138A to RHS 138B.

*Length*.—3.1 cm.

*Width*.—2.0 cm.

*Shape*.—Ovate.

*Base shape*.—Shortly attenuate.

*Apex shape*.—Apiculate.

*Margin*.—Dentate, Pinnatifid.

*Texture, upper surface*.—Slightly glossy, with sparse, short hair.

*Lower surface*.—Short, stiff hair mainly along the veins; some glandular hairs.

*Color of veins, upper surface*.—RHS 144D.

*Color of veins, lower surface*.—RHS 145C.

*Petiole color*.—RHS 145D; with RHS 145C on the under side.

*Length*.—0.7 cm.

*Diameter*.—0.4 cm.

*Texture*.—Hirtellous.

Stem:

*Characteristics*.—Side branches develop potentially at every node.

*Color of stem*.—RHS 143C.

*Length of stem*.—Approximately 0.15 cm.

*Diameter*.—0.2 cm.

*Length of internodes*.—Approximately 2.5-4.0 cm.

*Texture*.—Rough; densely covered with hair; hirsute.

*Color of peduncle*.—RHS 143C.

*Length of peduncle*.—Most often 2.0-6.0 cm.

*Peduncle diameter*.—0.2 cm.

*Texture*.—Rough, densely covered with short glandular hair; hirtellous.

Inflorescence:

*Type*.—Umbel-like, but actually a spike, umbrella-shaped to roughly semi-spherical.

*Blooming habit*.—Flowers continuously.

*Quantity of inflorescences per plant*.—17-21.

*Lastingness of individual blooms on the plant*.—About 4 days in the greenhouse.

*Fragrance*.—None.

*Inflorescence horizontal diameter*.—6.0 cm.

*Inflorescence depth* (*height*).—3.5 cm.

*Quantity of flowers and buds per inflorescence*.—21.

Bud (just when starting to show color):

*Color*.—RHS 47D.

*Length*.—2.4 cm.

*Width*.—1.1 cm.

*Shape*.—Mainly tube-shaped with a bulbous end.

Floret:

*Form and type*.—Sessile; salverform, composed of 5 partly fused petals with a base of a narrow tube.

*Immature color, upper surface*.—RHS 43C to RHS 43D.

*Lower surface*.—RHS 41D.

*Mature color, upper surface*.—RHS 33C to RHS 33D.

*Lower surface*.—RHS 32D.

*Floret diameter*.—2.0 cm.

*Floret depth*.—1.4-2.0 cm.

*Length of petals*.—1.0 cm.

*Width of petals*.—1.0 cm.

*Petal shape*.—Obcordate.

*Apex shape*.—Emarginate.

*Margin*.—Entire.

*Petal texture, upper surface*.—Smooth and glabrous.

*Lower surface*.—Smooth and glabrous.

*Corolla tube length*.—1.4-2 cm.

*Corolla tube color inside*.—RHS 150C.

*Tube color outside*.—RHS 145C.

*Corolla texture, inside*.—Glabrous.

*Outside*.—Glabrous basally; glandular hairs at the flare.

Calyx:

*Type*.—Five sepals whose margins are fused to each other along their length, with a transparent membrane of less than 0.1 cm in width and with one smaller sepal attached to the base of the calyx.

*Color of sepals*.—RHS 141C.

*Length of sepals*.—1.3 cm.

*Width of sepals*.—0.2 cm.

*Sepal shape*.—Linear, fused.

*Apex shape*.—Apiculate.

*Margins*.—Entire.

*Texture*.—Densely covered with short hair.

Reproductive organs:

*Pistil quantity*.—1.

*Length*.—1.5 cm.

*Style color*.—RHS 145D to 143C near the stigma.

*Style length*.—1.4 cm.

*Stigma color*.—RHS 143B.

*Stamens*.—Anthers and filaments fused to upper half of corolla tube; four anthers with two pollen sacs per anther.

*Color of filaments*.—RHS 150D to RHD 155B.

*Length filaments*.—0.1 cm.

*Anther color*.—RHS N154B.

*Length of anthers*.—0.1-0.15 cm.

*Color of pollen*.—RHS 1B.

*Pollen amount*.—Little.

*Fertility/seed set*.—Has not been observed on this hybrid.

*Disease/pest resistance*.—Has not been observed on this hybrid.

What is claimed is:

1. A new and distinct variety of *Verbena* plant named 'VEAZ0003' substantially as illustrated and described herein.

* * * * *